(12) United States Patent
Anderson et al.

(10) Patent No.: US 7,192,434 B2
(45) Date of Patent: Mar. 20, 2007

(54) VASCULAR PROTECTION DEVICES AND METHODS OF USE

(75) Inventors: Kent D. Anderson, Champlin, MN (US); John Oslund, Blaine, MN (US); Richard S. Kusleika, Eden Prairie, MN (US); Daniel O. Adams, Long Lake, MN (US)

(73) Assignee: ev3 Inc., Plymouth, MN (US)

( * ) Notice: Subject to any disclaimer, the term of this patent is extended or adjusted under 35 U.S.C. 154(b) by 522 days.

(21) Appl. No.: 10/132,562

(22) Filed: Apr. 25, 2002

(65) Prior Publication Data

US 2003/0171771 A1      Sep. 11, 2003

Related U.S. Application Data

(63) Continuation-in-part of application No. 10/093,572, filed on Mar. 8, 2002, now Pat. No. 6,773,448.

(51) Int. Cl.
*A61M 29/00* (2006.01)

(52) U.S. Cl. ..................................... 606/200

(58) Field of Classification Search ............... 606/127, 606/113, 114, 159, 200
See application file for complete search history.

(56) References Cited

U.S. PATENT DOCUMENTS

| | | |
|---|---|---|
| 4,643,184 A | 2/1987 | Mobin-Uddin |
| 4,790,812 A | 12/1988 | Hawkins et al. |
| 5,171,233 A | 12/1992 | Amplatz et al. |
| 5,192,286 A | 3/1993 | Phan et al. |
| 5,649,953 A | 7/1997 | Lefebvre |
| 5,725,552 A | 3/1998 | Kotula et al. |
| 5,814,064 A | 9/1998 | Daniel et al. |
| 6,129,739 A | 10/2000 | Khosravi |
| 6,179,859 B1 * | 1/2001 | Bates et al. ............. 606/200 |
| 6,290,710 B1 | 9/2001 | Cryer |
| 6,325,815 B1 | 12/2001 | Kusleika et al. |
| 6,371,969 B1 | 4/2002 | Tsugita et al. |
| 6,371,971 B1 | 4/2002 | Tsugita et al. |
| 6,383,196 B1 | 5/2002 | Leslie et al. |
| 6,607,506 B2 | 8/2003 | Kletschka |
| 2001/0012951 A1 | 8/2001 | Bates et al. |

(Continued)

FOREIGN PATENT DOCUMENTS

EP      1 127 556 A2      8/2001

(Continued)

OTHER PUBLICATIONS

Claims for U.S. Appl. No. 08/748,066, Mazzocchi et al., Nov. 12, 1996.

(Continued)

*Primary Examiner*—Kevin T. Truong
(74) *Attorney, Agent, or Firm*—Popovich, Wiles & O'Connell, P.A.

(57) ABSTRACT

An embolic protection device or system for use in a lumen of a vessel in a patient's vascular system. The device filters debris and blood clots in a body lumen and/or prevents them from moving distally from a treatment site in a vessel and causing emboli. The device may include a filter placed distally of the treatment site. The device may include an occlusive element placed either distally or proximally of the treatment site.

4 Claims, 13 Drawing Sheets

U.S. PATENT DOCUMENTS

2001/0041908 A1    11/2001    Levinson et al.
2002/0123765 A1    9/2002    Sepetka et al.
2002/0143360 A1    10/2002    Douk et al.

FOREIGN PATENT DOCUMENTS

| EP | 1 181 900 A2 | 2/2002 |
|----|----|----|
| WO | WO 96/01591 | 1/1996 |
| WO | WO 98/38443 | 9/1998 |
| WO | WO 00/16705 | 3/2000 |
| WO | WO 00/53120 | 9/2000 |
| WO | WO 01/08743 | 2/2001 |
| WO | WO 01/15629 | 3/2001 |
| WO | WO 01/21100 | 3/2001 |
| WO | WO 01/35857 A1 | 5/2001 |
| WO | WO 01/80777 | 11/2001 |
| WO | WO 01/87183 A2 | 11/2001 |

OTHER PUBLICATIONS

Claims for U.S. Appl. No. 10/051,565, Mazzocchi et al., Jan. 18, 2002.

Claims for U.S. Appl. No. 10/051,492, Mazzocchi et al., Jan. 18, 2002.

Claims for U.S. Appl. No. 10/051,591, Mazzocchi et al., Jan. 18, 2002.

Claims for U.S. Appl. No. 10/051,537, Mazzocchi et al., Jan. 18, 2002.

Claims for U.S. Appl. No. 10/051,648, Mazzocchi et al., Jan. 18, 2002.

Claims for U.S. Appl. No. 10/060,272, Mazzocchi et al., Jan. 30, 2002.

Claims for U.S. Appl. No. 10/060,271, Kusleika et al., Jan. 30, 2002.

Claims for U.S. Appl. No. 09/824,910, Kusleika et al., Apr. 3, 2001.

Claims for U.S. Appl. No. 10/060,854, Kusleika et al., Jan. 30, 2002.

U.S. Appl. No. 10/093,572, Kusleika et al., Mar. 8, 2002.

U.S. Appl. No. 10/194,355, Adams et al., Jul. 12, 2002.

U.S. Appl. No. 10/194,734, Kusleika, Jul. 12, 2002.

U.S. Appl. No. 10/096,624, Kusleika et al., Mar. 12, 2002.

\* cited by examiner

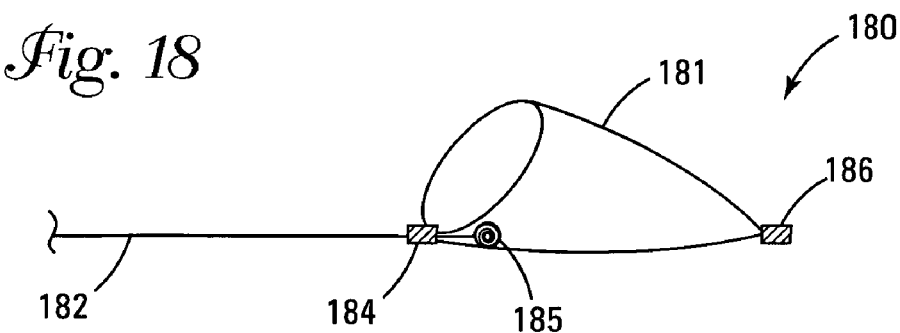
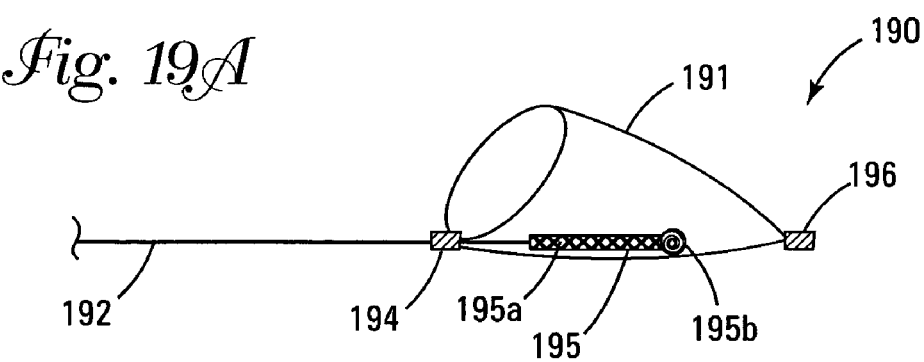
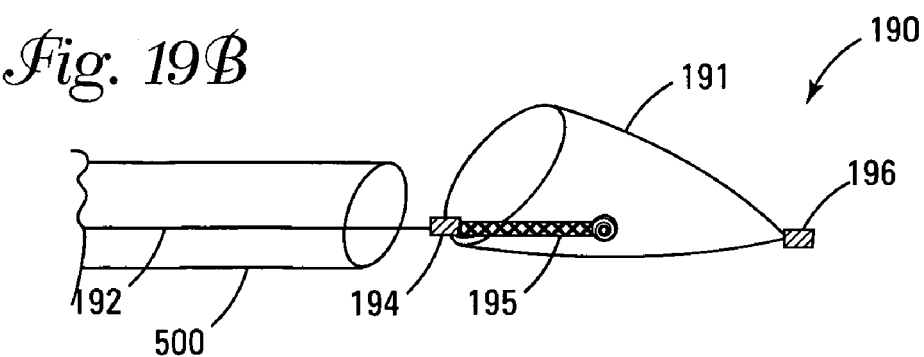

VASCULAR PROTECTION DEVICES AND METHODS OF USE

This application is a continuation-in-part of U.S. patent application Ser. No. 10/093,572 filed Mar. 8, 2002, now U.S. Pat. No. 6,773,448 issued Aug. 10, 2004, the disclosure of which is incorporated in its entirety herein by reference.

FIELD OF THE INVENTION

This invention relates to devices used in a blood vessel or other lumen in a patient's body.

BACKGROUND OF THE INVENTION

During vascular surgery or endovascular treatment of vessels including atherectomy, balloon angioplasty, and/or stent deployment, debris such as plaque and blood clots can move from the treatment site through a vein or artery, thus compromising the flow of blood at a location distal from the treatment site. Various distal protection systems have been developed to prevent such debris from embolizing in the vessel. Such distal protection devices include filters and occlusive devices, (e.g., balloons) placed distally of the treatment site.

It is desirable to place a distal protection device at a chosen location in order to achieve good sealing between the device and the wall of the vessel. Frequently it is necessary to match the protection device diameter with the vessel diameter, and vessels are known to taper or to have diameters that vary due to disease. It is also desirable to place the protection device in a relatively disease free portion of the vessel so as to minimize liberation of emboli from the wall of the vessel due to interaction with the protection device. Further, it is desirable that the device remains at the desired location during the procedure.

Distal protection devices typically are mounted on a wire or tube that functions as a guidewire. The distal protection devices are either fixedly attached to the guidewire or attached so as to permit a limited amount of motion between the device and the guidewire. Frequently, the same guidewire used to carry the device is also used to guide various catheters to and from the treatment site. For example, during the procedure, catheters may be exchanged over this guidewire.

The wire or tube comprising the guidewire typically passes through or alongside the filter and terminates in an atraumatic tip. This arrangement helps assure correct deployment of the distal protection device. A disadvantage to this, however, is that a continuous wire or tube has a stiffness that can cause vessel damage. Inadvertent axial motion of the wire or tube can also dislodge emboli. Because the wire or tube is stiff, the vessel within which it resides can be forced to take on its shape and become straightened. This is undesirable as this stresses the vessel. Further, the wire can press against the protection device disrupting the apposition of the device to the vessel. This can result not only in damage to the vessel but in dissection of the vessel. In addition, a stiff wire or tube, while desirable in controlling placement of a distal protection device, can prevent navigation of the device through tortuous anatomy.

Many distal protection devices such as the one shown in FIGS. 1A and B utilize a filter having a distal end that slides over or along an elongate support member SM such as a guidewire. The filter F is shown in its expanded deployed configuration in FIG. 1A and in its contracted delivery configuration in FIG. 1B. In these devices the distal end is at a first position with respect to the elongate support member when the filter is in its contracted delivery configuration and at a second more proximal position when the filter is in its expanded deployed configuration. In these designs, the length of the elongate support member that extends distally of the distal end of the filter must be increased by an amount S equal to the distance between the first and second positions to accommodate the slideable distal end of the filter. This increased elongate support member length distal to the filter can be a disadvantage for the reasons set forth above. In addition, this increased elongate support member length can prevent the filter from being used in connection with the treatment of distal lesions in the vascular anatomy since placement of the filter at a location distal to the treatment site may not be possible.

Thus, there is need in the art for a distal protection device that would avoid vessel damage and excessive vessel straightening while at the same time providing for distal vessel placement and superior navigation through tortuous anatomy.

SUMMARY OF THE INVENTION

This invention is an embolic protection device or system for use in a lumen of a vessel in a patient's vascular system. The device filters debris and blood clots in a body lumen and/or prevents them from moving distally from a treatment site in a vessel and causing embolization. In some embodiments the device which includes a filter is placed distally of the treatment site and in other embodiments which include an occlusive element the device is placed either distally or proximally of the treatment site.

In one embodiment, this invention is a protection device for filtering fluid flowing through a lumen of a vessel in a patient's vascular system, comprising an elongate support member having a proximal elongate segment and a distal elongate segment, the proximal and distal elongate segments each having proximal and distal ends. At least a distal portion of the distal elongate segment may comprise a flexible tip configured to navigate bends in the vessel. A filter element is carried by the elongate support member, the filter element being expandable from a delivery configuration to an expanded deployed configuration when the filter element is deployed in the body lumen. The filter element has a proximal end and a distal end, the proximal end of the filter element being connected at the distal end of the proximal elongate support segment and the distal end of the filter element being connected at the proximal end of the distal elongate support segment. The filter element has a body defining an interior cavity, the body having a plurality of openings configured such that when the filter element is in its deployed configuration within the vessel lumen particles within the fluid having a dimension above about 40 microns will be captured inside the cavity of the filter element. The body of the filter element defines a proximally facing opening into the cavity when the filter element is in the expanded deployed configuration. The proximally facing opening is large enough to allow blood along with debris/emboli from the treatment site to enter the cavity of the filter. The body may comprise a plurality of struts, and at least a distal portion of the struts may be covered with a filter mesh. The filter mesh is configured to capture particles of 40 to 500 microns. The proximal elongate segment may have a lumen which can be configured for delivery of a drug or for suctioning fluid from the body lumen. The body of the filter element may include a peripheral lip connected to a plurality of tethers. The protection device may also include a flexible connector having a first end connected at the distal end of the proximal elongate segment and a second end connected at the proximal end of the distal elongate segment.

The protection device may be configured such that no substantial portion of the elongate support member lies within the interior cavity of the filter.

In another embodiment, this invention is a protection device for use in a body lumen wherein the distal end of the proximal elongate support segment is spaced a first distance from the proximal end of the distal elongate support segment when the filter element is in its delivery configuration and a second distance from the proximal end of the distal elongate support segment when the filter element is in its expanded deployed configuration, the first distance being greater than the second distance.

In a further embodiment, this invention is a protection device for use in a body lumen having a functional element carried by the elongate support member and being expandable from a delivery configuration to a deployed configuration. The proximal end of the functional element is connected at the distal end of the proximal elongate support segment and the distal end of the functional element is connected at a location distal to the proximal end of the distal elongate support segment such that the proximal end of the distal elongate support segment is contained within a lumen of the proximal elongate segment when the functional element is in the delivery configuration and when the functional element is in the expanded deployed configuration. The functional element may comprise a filter or an occlusive element, for example, a balloon.

In one embodiment, this invention is a protection device for use in a body lumen comprising an elongate support member having an enlarged distal end. A slider is slideable over the elongate support member and is sized such that the enlarged distal end of the elongate support member limits movement of the slider in a distal direction. A functional element is carried by the elongate support member, the functional element being expandable from a delivery configuration to an expanded deployed configuration when the functional element is deployed in the body lumen. The functional element has a proximal end and a distal end, the proximal end of the functional element being connected to the slider. The functional element has a body defining a cavity, the enlarged distal end of the elongate support member being contained within the cavity.

In another embodiment, this invention is a protection device for use in a body lumen comprising an elongate support member having proximal and distal ends and a stop positioned proximally of the distal end which divides the elongate support member into proximal and distal portions. A proximal slider is slideable over the proximal portion of the elongate support member. The stop limits movement of the slider in a distal direction. A distal slider is slideable over the distal portion of the elongate support member. A functional element is carried by the elongate support member, the functional element being expandable from a delivery configuration to an expanded deployed configuration when the functional element is deployed in the body lumen. The functional element has a proximal end and a distal end. The proximal end of the functional element is connected to the proximal slider. The distal end of the functional element is connected to the distal slider. The functional element has a body defining a cavity, the distal end of the elongate support member being contained within the cavity and being slideably received by the distal slider when the functional element is in the delivery configuration and when the functional element is in the expanded deployed configuration.

In a further embodiment, this invention is a protection device for occluding the flow of fluid through a lumen of a vessel in a patient's vascular system comprising an elongate support member having a proximal elongate segment and a distal elongate segment. The proximal and distal elongate segments each have proximal and distal ends. An occlusive element is carried by the elongate support member, the occlusive element being expandable from a delivery configuration to an expanded deployed configuration when the occlusive element is deployed in the body lumen. The occlusive element has a proximal end and a distal end. The proximal end of the occlusive element is connected at the distal end of the proximal elongate support segment and the distal end of the occlusive element is connected at the proximal end of the distal elongate support segment. The occlusive element has a body substantially impervious to fluid flow such that when the occlusive element is in its deployed configuration within the vessel lumen the flow of the fluid through the lumen is substantially blocked.

In another embodiment, this invention is a protection device having an occlusive element carried by an elongate support member. The occlusive element has a body defining an interior cavity. The occlusive element is expandable from a delivery configuration to an expanded deployed configuration when the occlusive element is deployed in the body lumen. The occlusive element has a proximal end and a distal end. The proximal end of the occlusive element is connected at the distal end of the proximal elongate support segment and the distal end of the occlusive element is connected at the proximal end of the distal elongate support segment such that no substantial portion of the elongate support member lies within the cavity. The distal end of the proximal elongate support segment is spaced a first distance from the proximal end of the distal elongate support segment when the occlusive element is in its delivery configuration and a second distance from the proximal end of the distal elongate support segment when the occlusive element is in its expanded deployed configuration. The first distance is greater than the second distance. The protection device may be configured to be accommodated within a lumen of a catheter having a tubular shape with an exterior surface having an exterior diameter and an interior surface having an interior diameter. The distal elongate support segment may have a distal tip adjacent the distal end of the occlusive element. The distal tip has a first portion which may taper in a distal direction from a first diameter to a second diameter, the first diameter being larger than the second diameter. The first diameter may be larger or smaller than the interior diameter of the catheter.

In a further embodiment, the invention is a method of filtering emboli from blood flowing through the lumen of a vessel during a percutaneous procedure performed with a treatment device at a treatment site in the vessel. The method includes providing a treatment device having a filter carried on an elongate support member in accordance with the embodiments set forth above. The elongate support member and filter in its restrained delivery configuration are introduced into the lumen of the vessel and advanced until the filter is positioned at a desired location distal to the treatment site. The filter is expanded to its deployed configuration by removing the restraint. The treatment device is advanced over the elongate support segment to the treatment site while holding the proximal end of the proximal elongate segment. The percutaneous procedure is performed at the treatment site and any emboli dislodged during the treatment is filtered by the filter. The step of removing the restraint on the filter may be performed either before or after advancing the treatment device.

In another embodiment, the invention is a method of occluding blood flow through the lumen of a vessel during a percutaneous procedure performed with a treatment device at a treatment site in the vessel. The method includes providing an occlusive device carried on an elongate support member in accordance with any of the above embodiments. The elongate support member and occlusive device in its delivery configuration are introduced into the lumen of the vessel and advanced to a desired location distal to the treatment site. The occlusive device is expanded to its deployed configuration to occlude the lumen of the vessel. The treatment device is advanced through the vessel lumen over the elongate support member to the treatment site while holding the elongate support member. The percutaneous procedure is performed at the treatment site while the vessel lumen is occluded. The step of removing the restraint on the occlusive device may be performed before or after the treatment device is advanced. The method may include removing emboli from the blood in the occluded vessel through a lumen in the proximal elongate segment, the lumen having a first part positioned to be outside the patient's body when the occlusive device is deployed and a second port positioned proximal to the occlusive device.

In a further embodiment the invention is a protection device for filtering blood flowing through a lumen of a vessel in a patient's vascular system. The device includes an elongate support member having a proximal elongate segment and a distal elongate segment. The proximal and distal elongate segments each have proximal and distal ends, at least a distal portion of the distal elongate segment comprising a flexible tip configured to navigate bends in the vessel. A self-expandable filter element is carried by the elongate support member, the filter element being expandable from a delivery configuration to an expanded deployed configuration when the filter element is deployed in the body lumen. The filter element has a proximal end and a distal end, the proximal end of the filter element being connected to the proximal elongate support segment and the distal end of the filter element being connected to the distal elongate support segment. The filter element has a body defining an interior cavity, the device being configured so that no substantial portion of the elongate support member is contained within the interior cavity. The proximal end of the distal elongate support segment is distal to the distal end of the proximal elongate support segment when the filter element is in its delivery configuration and when the filter element is in its deployed configuration. The body has a plurality of openings configured such that when the filter element is in its deployed configuration within the vessel lumen particles within the fluid having a dimension above about 40 microns will be captured inside the cavity of the filter element.

In another embodiment the invention is a protection device for occluding the flow of blood through a lumen of a vessel in a patient's vascular system. The device has an elongate support member which includes a proximal elongate segment and a distal elongate segment, each having proximal and distal ends. An occlusive element is carried by the elongate support member. The occlusive element is expandable from a delivery configuration to an expanded deployed configuration when the occlusive element is deployed in the body lumen. The occlusive element has a proximal end and a distal end, the proximal end of the occlusive element being connected to the proximal elongate support segment and the distal end of the occlusive element being connected to the distal elongate support segment. The occlusive element has a body defining an interior cavity and is constructed so that no substantial portion of the elongate support member is contained within the interior cavity. The proximal end of the distal elongate support segment is distal to the distal end of the proximal elongate support segment when the occlusive element is in its delivery configuration and when the occlusive element is in its deployed configuration. The body is substantially impervious to fluid flow such that when the occlusive element is in its deployed configuration within the vessel lumen the flow of the blood through the lumen is substantially blocked.

In another embodiment the invention is an embolic protection system for filtering blood flowing through a lumen of a vessel in a patient's vascular system. The system includes a sheath having a lumen. The system further includes an elongate support member configured to be slideably received in the lumen of the sheath. The elongate support member has a proximal elongate segment and a distal elongate segment, the proximal and distal elongate segments each having proximal and distal ends. At least a distal portion of the distal elongate segment comprises a flexible tip configured to navigate bends in the vessel. A self-expandable filter element is carried by the elongate support member, the filter element being expandable from a delivery configuration when the filter element is constrained in the lumen of the sheath to an expanded deployed configuration when the filter element is deployed in the body lumen. The filter element has a proximal end and a distal end, the proximal end of the filter element being connected to the proximal elongate support segment and the distal end of the filter element being connected to the distal elongate support segment. The filter element has a body defining an interior cavity and is configured so that no substantial portion of the elongate support member is contained within the interior cavity. The proximal end of the distal elongate support segment is distal to the distal end of the proximal elongate support segment when the filter element is in its delivery configuration and when the filter element is in its deployed configuration. The body has a plurality of openings configured such that when the filter element is in its deployed configuration within the vessel lumen particles within the blood having a dimension above about 40 microns will be captured inside the cavity of the filter element.

In another embodiment the invention is an embolic protection system for occluding the flow of blood through a lumen of a vessel in a patient's vascular system. The system includes a sheath having a lumen and an elongate support member configured to be slideably received in the lumen of the sheath. The elongate support member has a proximal elongate segment and a distal elongate segment, the proximal and distal elongate segments each having proximal and distal ends. An occlusive element is carried by the elongate support member, the occlusive element being expandable from a delivery configuration when the occlusive element is contained within the lumen of the sheath to an expanded deployed configuration when the occlusive element is deployed in the body lumen. The occlusive element has a proximal end and a distal end, the proximal end of the occlusive element being connected to the proximal elongate support segment and the distal end of the occlusive element being connected to the distal elongate support segment. The occlusive element has a body defining an interior cavity which is configured such that no substantial portion of the elongate support member is contained within the interior cavity. The proximal end of the distal elongate support segment is distal to the distal end of the proximal elongate support segment when the occlusive element is in its delivery configuration and when the occlusive element is in its deployed configuration. The body of the occlusive element is substantially impervious to fluid flow such that when the occlusive element is in its deployed configuration within the vessel lumen the flow of the blood through the lumen is substantially blocked.

In a further embodiment the invention is a protection device for use in the lumen of a vessel in a patient's vascular system. The device includes an elongate support member having a proximal end and a distal end and a functional element carried by the elongate support member. The functional element is expandable from a delivery configuration to an expanded deployed configuration when the functional element is deployed in the lumen of the vessel. The functional element has proximal and distal ends; the proximal end is connected to the distal end of the elongate support member, the distal end is radiopaque and shaped to be atraumatic. The functional element has a body defining a cavity and no substantial portion of the elongate support member is contained within the cavity.

In another embodiment, the invention is a protection device for use in a body lumen. The device comprises an elongate support member having a proximal elongate segment and a distal elongate segment. The proximal and distal elongate segments each have proximal and distal ends, and the distal end of the proximal elongate segment is enlarged. A slider is slideable over the proximal elongate segment, and the enlarged distal end of the proximal elongate segment limits movement of the slider in a distal direction. A functional element is carried by the elongate support member, and is expandable from a delivery configuration to an expanded deployed configuration when the functional element is deployed in the body lumen. The functional element has a proximal end connected to the slider, and it has a distal end. The functional element has a body defining a cavity and the enlarged distal end of the proximal elongate segment is contained within the cavity.

The functional element may comprise a filter or an occlusive element, which may comprise a balloon. The functional element may comprise a body defining an interior cavity and wherein no substantial portion of the elongate support segment lies within the interior cavity. The body may comprise a plurality of struts and at least a distal portion of the struts may be covered with an occlusive material.

In another embodiment, the invention is a method of filtering emboli from blood flowing through the lumen of a vessel during a percutaneous procedure performed with a treatment device at a treatment site in the vessel. The method includes providing an embolic protection system including a catheter configured to slideably receive an elongate support member having proximal and distal elongate segments, each having proximal and distal ends, and a self-expandable filter carried by the elongate support member. The filter is expandable from a delivery configuration when the filter is restrained inside the catheter to an expanded deployed configuration when the filter is deployed beyond a distal end of the catheter. The filter has proximal and distal ends. The proximal end of the filter is connected at the distal end of the proximal elongate segment and the distal end of the filter is connected at the proximal end of the distal elongate segment. The filter element has a body defining an interior cavity, the body having a plurality of openings configured such that when the filter is in its deployed configuration within the vessel particles within the blood having a dimension above about 40 microns will be captured inside the cavity of the filter. The method includes introducing the catheter containing the elongate support member and filter in its delivery configuration into the lumen of the vessel; advancing the catheter through the vessel until the filter is positioned at a desired location distal to the treatment site, at least a proximal portion of the proximal elongate member extending outside of the vessel; deploying the filter out of the distal end of the catheter to expand the filter within the lumen of the vessel to its expanded deployed configuration; withdrawing the catheter from the vessel; advancing the treatment device over the elongate support member to the treatment site while holding the proximal elongate segment; performing the percutaneous procedure at the treatment site with the treatment device; and filtering emboli from blood during the percutaneous procedure with the filter.

In a further embodiment the invention is a method of occluding blood flow through the lumen of a vessel of a patient's body during a percutaneous procedure performed with a treatment device at a treatment site in the vessel. The method includes providing an embolic protection device including a catheter configured to slideably receive an elongate support member having proximal and distal elongate segments, each segment having proximal and distal ends, and an occlusive device carried by the elongate support member. The occlusive device is expandable from a delivery configuration when the occlusive device is contained within the catheter to a deployed configuration. The occlusive device has proximal and distal ends, the proximal end of the occlusive device being connected at the distal end of the proximal elongate segment and the distal end of the occlusive device being connected at the proximal end of the distal elongate segment. The occlusive device has a body substantially impervious to blood flow. The method includes introducing the catheter containing the elongate support member and the occlusive device in its delivery configuration into the lumen of the vessel; advancing the catheter through the vessel until the occlusive device is positioned at a desired location distal to the treatment site, at least a proximal portion of the proximal elongate segment extending outside of the vessel; extending the occlusive device beyond a distal end of the catheter; expanding the occlusive device to its deployed configuration to occlude the lumen of the vessel; withdrawing the catheter from the vessel; advancing the treatment device over the elongate support member to the treatment site while holding the proximal elongate segment; and performing the percutaneous procedure at the treatment site with the treatment device while the lumen of the vessel is occluded.

BRIEF DESCRIPTION OF THE DRAWINGS

FIG. 5C further illustrates the device loaded in a delivery catheter.

FIG. 12B additionally shows a connector between the proximal and distal elements.

FIG. 18 is a schematic view of an alternate embodiment of the device of this invention having a continuous elongate support member.

FIGS. 19A to 19C are schematic views of a further alternate embodiment of the device of this invention having a continuous elongate support member and illustrating motion of the device relative to a catheter.

DETAILED DESCRIPTION OF THE PREFERRED EMBODIMENTS

Figure 1A:
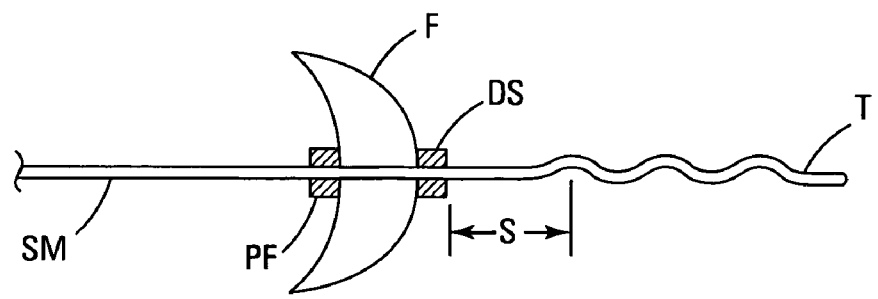
FIGS. 1A and 1B are schematic views of a Prior Art distal protection device showing an embolic filter carried by the device in its expanded deployed configuration and in its contracted delivery configuration, respectively.

Various embodiments of the invention are disclosed herein. Although the devices disclosed in the various embodiments described herein include embolic filters the present invention is also applicable to other types of functional devices including occlusive devices comprising inflatable balloons or filter-like framework structures coated with flexible polymer. In the case of an occlusive balloon device, it is advantageous to construct the device on a hollow elongate member so as to allow inflation and deflation of the balloon through the hollow member. Further, although the examples relate generally to protection devices deployed distal to a treatment site, the device can also be deployed proximal to a treatment site for the purpose of interrupting or reversing flow through the vessel. In the case of a proximally deployed device, it will be advantageous to construct the device on a hollow elongate member so as to preserve access to the treatment site through the hollow member.

The terms "distal" and "proximal" as used herein refer to the relative position of the guidewire, catheters, and distal protection system in a lumen. Thus, "proximal" refers to a location upstream from the "distal" position. That is, the flow of a body fluid, such as blood, moves from the proximal to the distal portions of the device of this invention.

The various embodiments of distal protection systems of this invention are meant to encompass the use of any functional device such as occlusive devices and filters designed to be deployed in a vessel of a patient in a minimally invasive procedure. Typically the distal protection system is introduced into a blood vessel through an introducing catheter. Methods of introducing guidewires and catheters and the methods for the removal of such devices from vessels are well known in the art of endovascular procedures. In a typical procedure using the device of this invention, the elongate support member and filter are loaded into an introducing sheath or catheter and moved into the vessel and through the catheter to the treatment site. This is done typically by advancing a first, or introduction guidewire, through the vessel to the region of interest. A catheter is advanced over the guidewire to the region of interest, and the guidewire removed. Then the filter or other functional device carried by the elongate support member is advanced down a catheter sheath to the region of interest but within the catheter. The catheter sheath is withdrawn to deploy (expand) the filter at the region of interest. Alternatively, the filter is preloaded into a catheter and held in place by an outer sheath of the catheter and they are together advanced through the vessel to the region of interest without using an initial guidewire. Then the catheter is withdrawn to deploy the filter. In a second alternative, an introduction guidewire is advanced to the region of interest, and the filter (contained in a catheter) is advanced over the guidewire to the region of interest, at which point the catheter is removed leaving the deployed filter near the region of interest on the guidewire.

Typical dimensions of a filter used in the devices of this invention range from 2 mm to 90 mm in length, and from about 0.5 mm to 2 mm in diameter before deployment, and about 2 mm to 30 mm in diameter after deployment. A typical guidewire is about 0.2 to 1.0 mm in diameter and ranges from 50 cm to 320 cm in length.

The protection device is made from biocompatible materials. Materials also may be surface treated to produce biocompatibility. The elongate support member may be formed of any material of suitable dimension, and generally comprises metal wire. Suitable materials include stainless steel, titanium and its alloys, cobalt-chromium-nickel-molybdenum-iron alloy (commercially available under the trade designation Elgiloy™), carbon fiber and its composites, and engineered polymers such as liquid crystal polymers, polyetheretherketone (PEEK), polyimide, polyester, and the like. A shape memory or superelastic metal such as nitinol is also suitable. The elongate support member may be solid or may be hollow over some or all of its length.

The material used to make the filter or filter support structure preferably is self-expanding. This can be accomplished by using self-expanding materials. These materials include metals such as stainless steel, titanium and its alloys, cobalt-chromium-nickel-molybdenum-iron alloy (commercially available under the trade designation Elgiloy™), carbon fiber and its composites, and engineered polymers such as liquid crystal polymers, polyetheretherketone (PEEK), polyimide, polyester, silk, and the like. A shape memory or superelastic metal is particularly suitable for those applications when it is desired for an element, such as a filter, to assume a pre-determined three-dimensional shape or for a guidewire to maintain a pre-determined curvature. A shape memory or superelastic metal comprising nickel and titanium known as "nitinol" is commercially available in various dimensions and is suitable for use as both a guidewire and a filter. For example, nitinol tubular braid can be heat set into a desired shape, compressed for delivery to a site, and then released to form the heat-set shape.

The filter element has a body defining an interior cavity. The filter body has a plurality of openings such that, when the filter element is in its deployed configuration within the vessel lumen, particles within the fluid are captured inside the interior cavity of the filter element. The filter may comprise any material that is suitably flexible and resilient, such as a mesh, i.e., a material having openings or pores. The filter may comprise braided, knitted, woven, or non-woven fabrics that are capable of filtering particles having dimension of 40 to about 500 microns. Non-woven fabrics may additionally be treated to fuse some or all of the fiber intersections. The fabric may be electrospun. Suitable material includes that formed from sheets, films, or sponges, polymeric or metallic, with holes formed by mechanical means such as laser drilling and punching, or by chemical means such as selective dissolution of one or more components. For example, a suitable filter material is braided tubular fabric comprising superelastic nitinol metal. Mesh fabric of nitinol material can be heat-set to a desired shape in its expanded configuration. The filter material is preferably at least partially radiopaque. The filter material can be made radiopaque by plating, or by using core wires, tracer wires, or fillers that have good X-ray absorption characteristics compared to the human body.

Some embodiments of the device include a sliding element, for example, at the proximal end of the filter. One type of sliding element comprises inner and outer annular rings. The first ring fits within the second ring. The inner diameter of the first ring is larger than the diameter of the elongate support member so that the sliding element can slide over the elongate support member. The sliding element can be affixed to the filter fabric by placing the fabric between the first and second rings. However, this is not meant to be limiting, and the filter fabric can also be affixed to the slideable element by adhesive, solder, crimping, or other means known in the art. The slider may comprise any stiff material such as metal or polymer and preferably the slider is radiopaque. Suitable materials include stainless steel, titanium, platinum, platinum/iridium alloy, gold alloy, polyimide, polyester, polyetheretherketone (PEEK), and the like.

Movement of a sliding element with respect to the elongate support member can be facilitated by coating one or both of the inside of the sliding element and the outside of the elongate support member with a friction-reducing coating, such as polytetrafluoroethylene (commercially available under the trade designation Teflon™) or a lubricious hydrophilic coating.

By "fixed element" is meant an element that is attached to the elongate support member and does not move independently of it. The fixed element may be an annular ring but also included within this meaning is an element that is crimped, adhered, soldered, or otherwise fastened directly to the elongate support member. Also, the filter fabric may be attached directly to the elongate support member. In any event, the sliding and fixed elements (or any attachment point) typically comprise radiopaque material to assist in the placement of the filter. In addition, one or more radiopaque markers may be positioned at various locations on the protection device. These radiopaque markers or marker bands comprise a material that will be visible to X-rays and they assist in positioning the device.

Some embodiments include a "floppy tip" at a distal portion of the distal elongate support segment. The floppy tip provides an atraumatic and radiopaque terminus for the device. An atraumatic tip prevents vessel injury during initial placement or subsequent advancement of the device. A radiopaque tip helps the physician verify suitable tip placement during fluoroscopy. The floppy tip preferably comprises a springy or resilient material, such as a metal (e.g., stainless steel, iron alloys such as Elgiloy™, and shape memory or superelastic metal such as nitinol) or polymer (e.g., polyetheretherketone (PEEK), polyimide, polyester, polytetrafluoroethylene (PTFE), and the like). Springy materials are desirable because they tend to retain their shape. The physician will initially 'shape'the tip, typically with a slight curve, and then as the device is advanced through the body the tip will be deflected as it encounters obstacles. It is desirable, after the inevitable deflections during insertion, that the tip restore itself to the pre set shape. Polymeric materials additionally may be reinforced with metals or other fillers. The material may be a monofilament or multifilament (such as a cable). The floppy tip may be tapered or have a uniform diameter over its length. The floppy tip may comprise a tube, or could have circular, flat, or other cross-sections. It may be coiled. The tip may comprise one or more elements (i.e., parallel independent structures). The tip may be polymer-coated or otherwise treated to make the surface slippery. The floppy tip can be any desired length.

Other elements of the filtration device also comprise biocompatible materials, and these include metals and polymeric materials. These materials can be treated to impart biocompatibility by various surface treatments, as known in the art. When wire is used, the wire is selected on the basis of the characteristic desired, i.e., stiffness or flexibility, and the properties can depend upon both the diameter of the wire and its cross-sectional shape. The size, thickness and composition of elastic materials are selected for their ability to perform as desired as well as their biocompatibility. It is to be understood that these design elements are all within the scope of this invention.

The various embodiments of the invention will now be described in connection with the drawing figures. It should be understood that for purposes of better describing the invention, the drawings have not been made to scale. Further, some of the figures include enlarged or distorted portions for the purpose of showing features that would not otherwise be apparent. The material comprising the filter (e.g., mesh or fabric with pores, as described above) is indicated by cross-hatching in some of the figures but is omitted from others for simplicity.

Figure 1B:
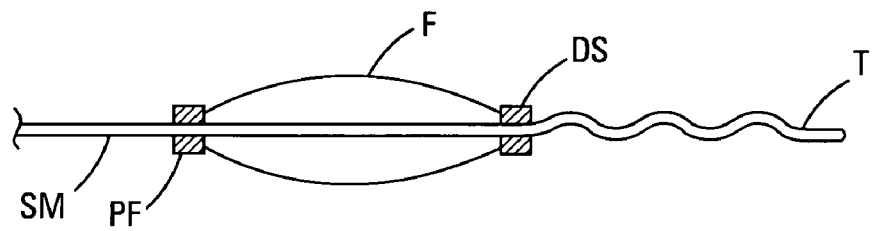

FIGS. 1A and 1B are schematic views of a prior art distal protection device having an elongate support member SM which carries a filter F. The proximal end of the filter is connected to a proximal fixed element PF and the distal end of the filter is connected to a distal slider DS. The proximal fixed element is connected at a fixed location on the elongate support member while the distal slider is configured to slide freely over the elongate support member. The elongate support member terminates distally at atraumatic floppy tip T. The filter is shown in its expanded deployed configuration in FIG. 1A and in its contracted delivery configuration in FIG. 1B. As best seen in FIG. 1A the distal slider travels over the elongate support member a distance S when the filter is contracted from the deployed to the delivery configuration. An example of such a filter is disclosed in WO 96/01591 (Mazzochi et al.).

FIGS. 2 to 15 are schematic views of various embodiments of a device which includes a discontinuous elongate support member carrying a functional element such as a filter or occlusive device. In these embodiments the elongate support member includes a proximal elongate support segment and a distal elongate support segment. The functional element has a proximal end connected at or near a distal end of the proximal elongate support segment and a distal end connected at or near a proximal end of the distal elongate support segment. The functional element has a body which defines an interior cavity. No substantial portion of the elongate support member lies within the cavity. What this means is that the protection device is constructed so that the functional element expands from its delivery configuration to its deployed configuration without interference between the distal and proximal elongate support elements. Specifically, when the functional element is deployed the distance between the distal and proximal ends of the functional element decreases. In most embodiments, but not necessarily all embodiments, when the functional element is fully expanded there is still distance between the distal and proximal ends of the element. Thus, although not shown in the drawing figures, this design permits some portion of the distal and/or proximal elongate support members to be within the cavity so long as the length or combined lengths of the portion(s) within the cavity do not exceed the distance between the distal and proximal ends of the functional element in its fully expanded configuration and thus there is no interference with the expansion and deployment of the functional element.

Figure 2A:
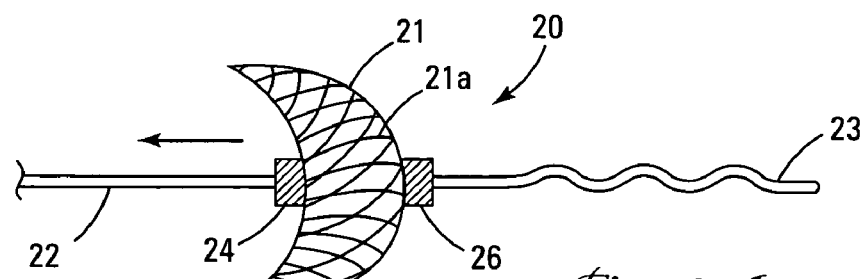
FIGS. 2A and 2B are schematic views of a first embodiment of the distal protection device of this invention including a discontinuous elongate member having proximal elongate support segment having a distal end which extends only to the proximal end of the filter and a distal elongate support segment which extends distally of the distal end of the filter.
Figure 2B:
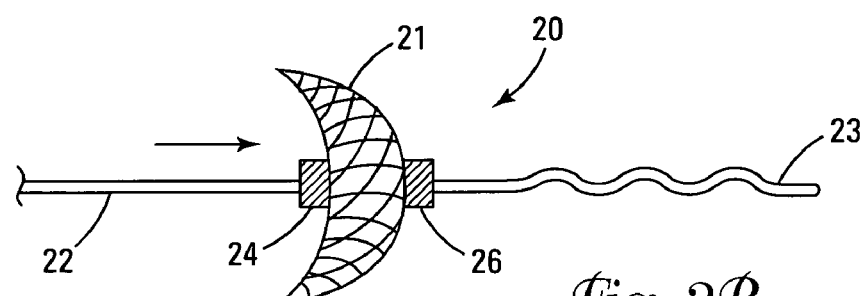

FIGS. 2A and 2B show a first embodiment of the protection device. Filter 21 is affixed to proximal fixed element 24 which is affixed to the distal end of proximal elongate support segment 22. Filter 21 has distal element 26 which is affixed to a distal elongate support segment including floppy tip 23. Floppy tip 23 is provided as an atraumatic terminus for the filter. Floppy tip 23 may optionally be radiopaque. The tip comprises any suitably flexible and springy material, as discussed above. Mesh 21a is indicated by cross-hatching in the figure. Both figures illustrate a deployed filter, but comparison of FIGS. 2A and 2B show how the filter shape changes and mesh 21a compresses when the proximal elongate support segment is moved distally relative to distal element 26 along the direction shown by the arrow in FIG. 2B. Comparing FIGS. 1A and 2A it is apparent that the distal elongate support segment 23 need not include the additional length S since distal element 26 is not required to slide over the elongate support member.

Figure 2C:
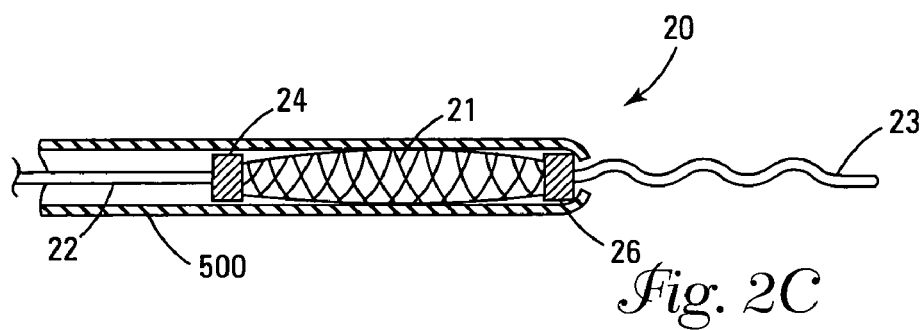
FIG. 2C is a cross-sectional view of the distal protection device of FIGS. 2A and 2B contained within a delivery catheter in a contracted delivery configuration.

FIG. 2C shows the filter of FIGS. 2A and 2B in its contracted delivery configuration contained in a delivery catheter 500. FIGS. 2A to 2C clearly show that although the distance between elements 24 and 26 varies from the delivery to the deployed configuration the distance between the distal element and the distal tip of the distal elongate support segment does not vary but remains constant at all times during the delivery and deployment of the filter. Thus, no additional length need be provided for the elongate support member extending distal to the filter to accommodate the differences in the distance between the proximal and distal elements.

During delivery, the catheter is advanced through a body lumen such as the lumen of a vessel until the filter is positioned at a desired location distal to a treatment site in the lumen. Positioning of the filter is facilitated by the floppy tip portion of the distal guidewire segment which allows the catheter to be maneuvered through even tortuous lumens. However, because of the unique design of the present invention, the distal segment is not required to be made longer than necessary or desired for efficient maneuverability. The filter is deployed by withdrawing catheter 500 proximally to expose the self-expanding filter. During expansion of the filter from the delivery configuration to the deployed configuration, the gap between the proximal end of the distal elongate support segment and the distal end of the proximal elongate support segment closes. The gap is closed by movement of the distal elongate support segment in a proximal direction caused by the expansion of the filter and/or by the physician moving the proximal elongate support segment in a distal direction.

Figure 2D:
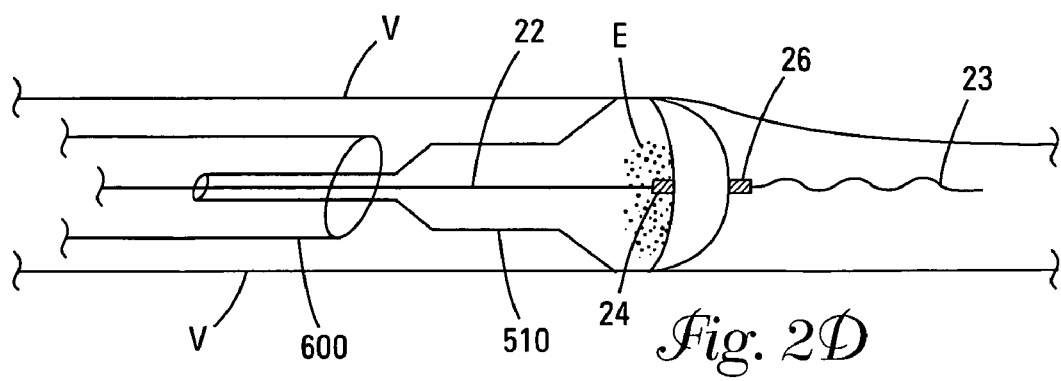
FIG. 2D is a schematic view of the distal protection device deployed in a vessel V and being recovered with a recovery catheter.

FIG. 2D shows a recovery system that could be used to remove a distal protection device such as the one shown in FIGS. 2A to 2C from a body lumen. System 30 includes a recovery catheter 600 and a funnel or cover 510. In use, the catheter 600 is advanced over the proximal elongate support segment toward the filter which has been used to capture emboli or other debris E during a treatment procedure in the lumen of a vessel V. During advancement the cover is contained within the lumen of the recovery catheter. At a desired location just proximal of the filter the cover is deployed by withdrawing the recovery catheter distally. The filter is then pulled into the cover by withdrawing the proximal elongate support segment proximally. During this procedure the filter may retain its general bell shape or may revert somewhat into an olive shape. In either case the captured emboli is retained because the self-expanding filter will maintain enough of an expanded shape against the walls of the body lumen to retain the emboli. The cover and filter are withdrawn into the recovery catheter and the recovery catheter, cover and filter are withdrawn from the body lumen. The cover assists in retaining emboli within the filter during the withdrawal process. The recovery catheter and cover are described more fully in WO 00/53120 (Kusleika et al).

Figure 3A:
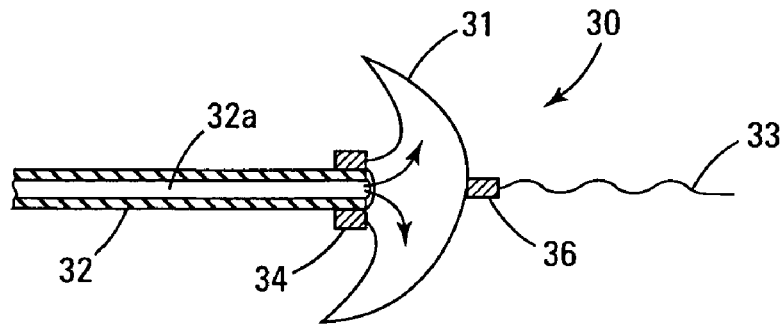
FIGS. 3A and 3B are schematic views of a further embodiment wherein the proximal elongate support segment is provided with a lumen for delivery of therapeutic agents (FIG. 3A) and for aspiration of emboli (FIG. 3B).

A similar elongate support member design can be incorporated into a variety of other embolic protection devices. The design of the present invention can be incorporated into protection devices having elongate support members or filters of varying configuration. Some of these various designs incorporating this embodiment are shown in FIGS. 3 to 17. For example, FIG. 3A is a schematic view in partial cross-section of device 30, in which filter 31 is affixed to a hollow proximal elongate support segment or tube 32 by proximal fixed element 34. Filter 31 has distal element 36 which is attached to a distal elongate support segment which includes floppy tip 33. Therapeutic agents, such as those used to treat arrhythmia of the heart, anti-restenotic agents, and anti-thrombotic or anti-platelet agents can be delivered through lumen 32a of tube 32 to the region of the filter.

Figure 3B:
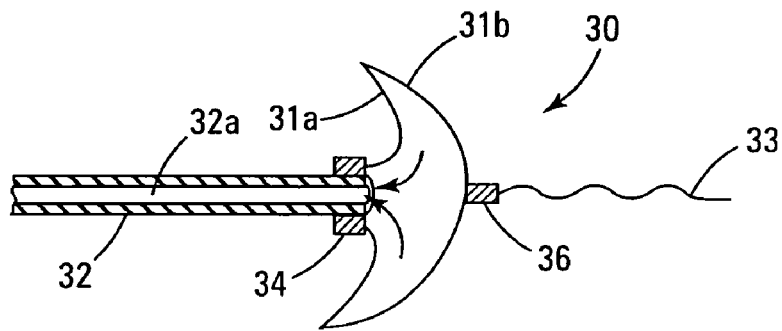

Alternatively, as shown is FIG. 3B, such an arrangement could be used to aspirate emboli and other debris from the filter region. Tube 32 in this case would likely have a larger diameter lumen than a tube used to deliver therapeutic agents. In order to efficiently aspirate emboli and debris from the treatment site the proximal face 31a of the filter may be provided with larger filter holes than the distal face 31b of the filter. Alternatively, the proximal face can be made of a mesh or other material with holes of sufficient size to enable emboli to flow into the filter between the proximal and distal faces and the distal face can be totally or partially occlusive such as by way of an occlusive coating or attached film. In either case this enables emboli to be aspirated into the tube and out of the lumen in the direction of the arrows in FIG. 3B.

Figure 3C:
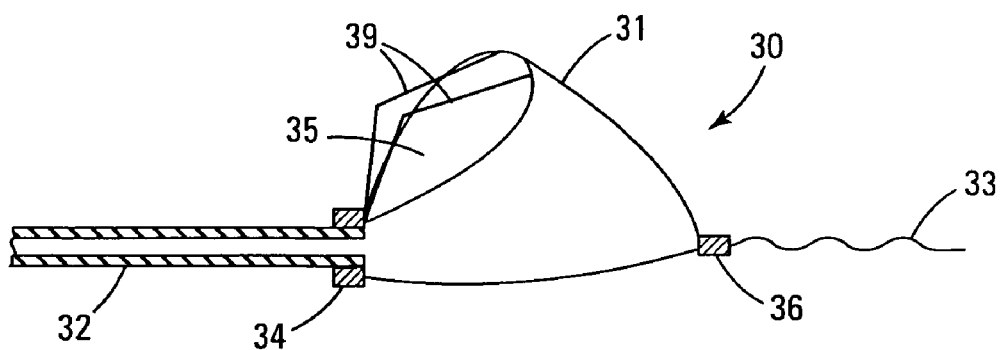
FIG. 3C is a schematic view of a device similar to that of FIG. 3B but with a differently shaped filter.

It should be noted that although a particular filter configuration is disclosed in the embodiments of FIGS. 3A and 3B, the concepts are equally applicable to other filter styles. For example, the embodiment of FIG. 3B could be constructed with a filter like the one disclosed in FIG. 12A. Such a configuration is shown in FIG. 3C, in which filter 31 is shown with two wire segments or loops 39. These loops or segments attach to the proximal end of the filter and serve to bias the filter and its opening 35 in its open or expanded configuration. The loops also serve to stabilize proximal element 34 against the lumen wall so as the prevent emboli from bypassing the filter due to motion of proximal elongate support segment 32.

FIGS. 4 to 10 illustrate various embodiments of the device of this invention wherein the filter comprises struts which assist in holding the filter mesh open and/or in collapsing the filter into a recovery catheter.

Figure 4A:
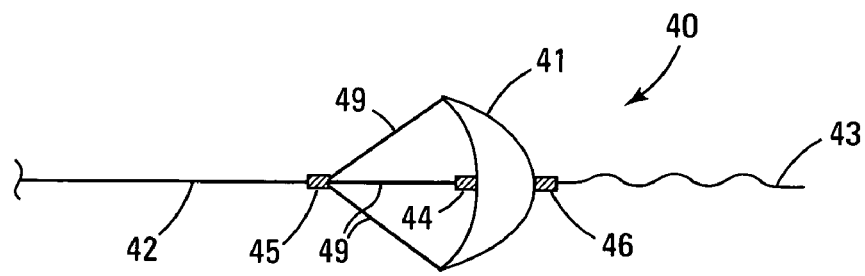
FIG. 4A is a schematic view of an alternate embodiment of the device of this invention wherein the filter includes tethers and FIGS. 4B to 4D illustrate motion of the device relative to a delivery catheter.

FIG. 4A shows device 40, in which the proximal end of filter 41 is affixed to proximal fixed element 44. Element 44 is affixed to proximal elongate support segment 42. The distal end of filter 41 is attached to distal element 46 to which is attached a distal elongate support segment including floppy tip 43. Filter element 41 is biased to self-expand and is shown in its expanded deployed configuration in FIG. 4A. Extending proximally from filter 41 are struts or tethers 49 which are affixed at one end to element 45. Element 45 is affixed to proximal guidewire segment 42 at a point proximal of element 44. The tethers are connected at their second end to a peripheral lip of filter 41 by welding, knotting, interweaving, traversing between the mesh layers, and the like. The struts or tethers permit recovery of the filter from a body lumen without the use of a separate funnel or cover.

Figure 4B:
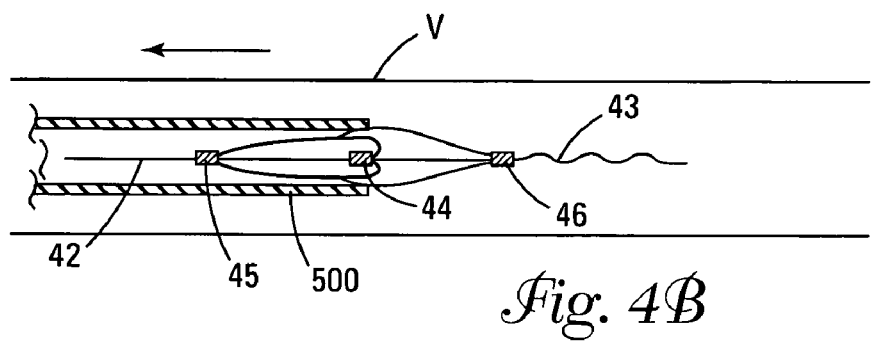

FIG. 4B illustrates device 40 within a delivery catheter 500. The device is loaded into the catheter by pulling the proximal elongate support segment proximally in the direction of the arrow until the filter is contained within the lumen of the delivery catheter. The device is used by advancing the delivery catheter through a body lumen until the distal end of the delivery catheter is at a desired location distal to the treatment site. The filter is then deployed in the body lumen. This can be done by withdrawing the delivery catheter proximally while maintaining the position of the filter or by advancing the filter distally while maintaining the position of the delivery catheter by advancing the proximal elongate support segment distally.

Figure 4C:
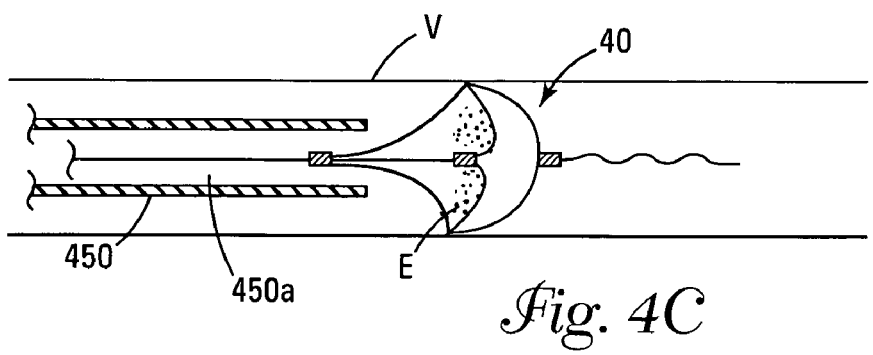
Figure 4D:
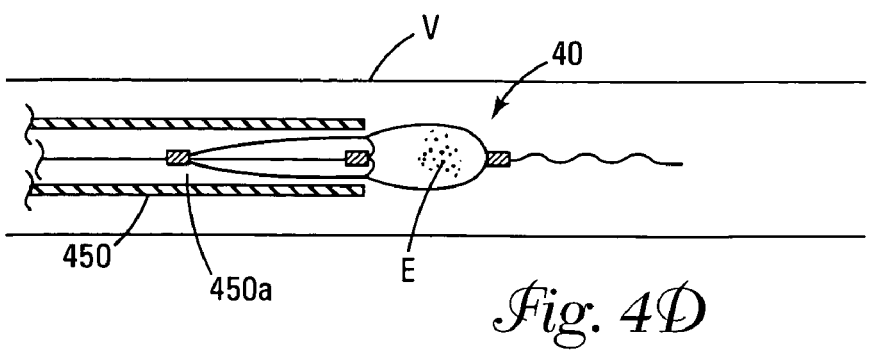

FIGS. 4C and 4D illustrate one way in which filter 41 may be recovered from the body lumen after capturing emboli E released during a treatment procedure. After the procedure the device can be recovered with the same catheter used to deliver the device or with a separate recovery catheter 450 which is usually slightly larger than the delivery catheter. The recovery catheter is advanced over the proximal elongate support segment. Once the distal end of the recovery catheter has been advanced distally of element 45 the tethers 49 are drawn into lumen 450a of the recovery catheter. This causes the peripheral lip of the filter to be drawn radially inwardly in the direction of the proximal elongate support segment. In FIG. 4C the peripheral lip is shown partially closed. In FIG. 4D the delivery catheter is shown advanced to a more distal position and the peripheral lip is drawn up to the distal end of the recovery catheter. It is possible to withdraw the recovery catheter, elongate support member and filter in the configuration shown in FIG. 4D or, alternatively, the delivery catheter may be advanced distally until the filter is contained entirely or partially within the delivery catheter before it is withdrawn from the body lumen.

Figure 5A:
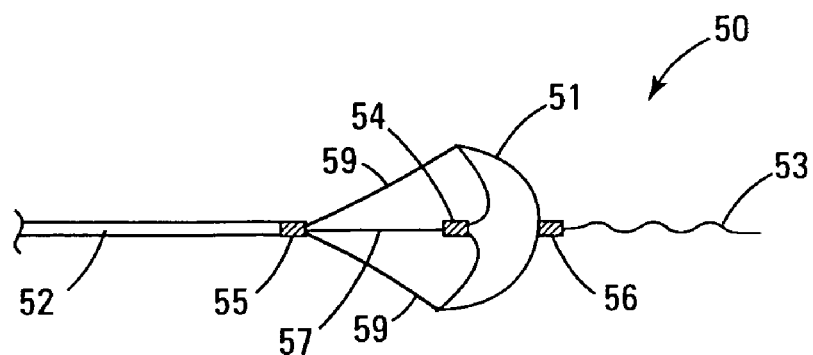
FIGS. 5A to 5C are schematic views of an alternate embodiment of the device of this invention wherein the filter includes tethers.
Figure 5B:
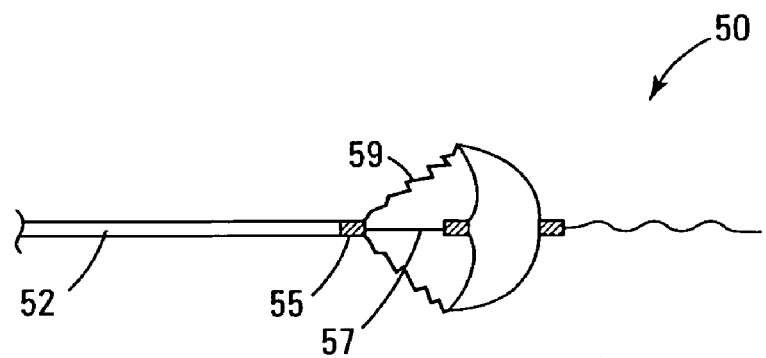
Figure 5C:
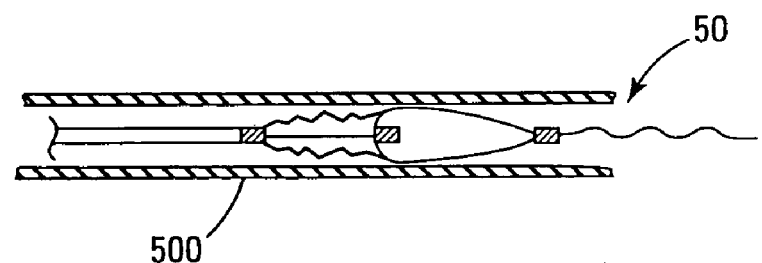

FIGS. 5A, 5B and 5C illustrate a device 50, similar to device 40, except that the tethers are connected at their proximal ends to a hollow tube which is moveable axially with respect to the elongate support member. Filter 51 is biased to self-expand and is affixed at its proximal end to proximal fixed element 54 which in turn is affixed to proximal elongate support segment 57. Filter 51 has distal element 56 that is attached to a distal elongate support segment including floppy tip 53. Extending proximally from a peripheral lip of filter 51 are struts or tethers 59 which are affixed at one end to the filter and at another end to element 55. Element 55 is affixed to hollow tube 52.

FIG. 5A shows the device in its expanded deployed configuration with the tube positioned with respect to the proximal elongate support segment so that there is no slack in the tethers. FIG. 5B shows the device in its deployed configuration but with the tube advanced distally so that there is slack in the tethers. FIG. 5C shows the device loaded in a delivery catheter 500. When loaded in the delivery catheter the tube may be positioned so the tethers are slack or so there is no slack in the tethers. The device is used by advancing the delivery catheter to a desired location distal to the treatment site. The delivery catheter is withdrawn proximally while the tube and proximal elongate support segment are held stationary to deploy the filter. If desired after deployment the tube can be withdrawn a short distance proximally to remove any slack from the tethers. After the treatment procedure has been performed in the body lumen, the filter is removed in a manner somewhat similar to that described with respect to FIG. 4. Prior to recovery any slack in the tethers is removed by moving the tube proximally. Then the delivery catheter or a separate larger recovery catheter is advanced distally over the proximal elongate support segment while the position of the tube and the proximal elongate support segment are maintained. In this manner the filter is drawn into the recovery catheter in the same manner as described above.

Figure 6:
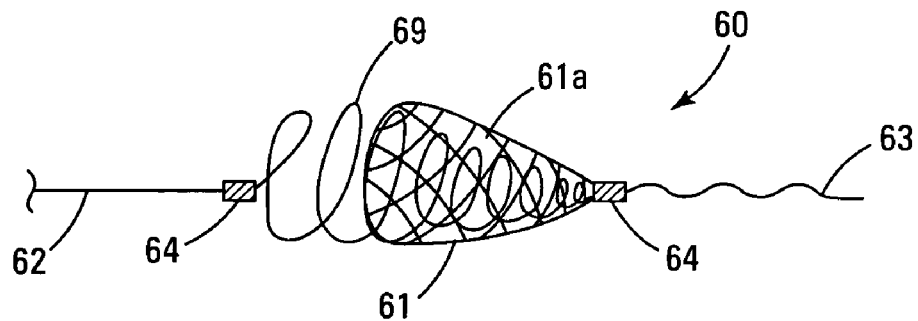
FIGS. 6 to 10 show further embodiments of the device of this invention wherein the filter comprises tethers or struts, at least a portion of which are covered by filter fabric.

The present invention which includes use of a discontinuous elongate support segment is equally applicable to other expandable functional devices including other filter structures, some of which are disclosed in FIGS. 6 to 10, which incorporate support struts, at least a distal portion of which are covered by a filter mesh. FIG. 6 illustrates device 60, wherein filter 61 comprises coiled strut 69, a distal portion of which is covered by filter fabric 61a (shown by cross-hatching). Alternatively, material 61a could be occlusive. Strut 69 is suitably elastic such that it will self-expand to contact the wall of a vessel after deployment of the filter from the distal end of a delivery catheter. Strut 69 is affixed to proximal fixed element 64 which in turn is affixed to proximal elongate support segment 62. Filter fabric 61a is attached to a portion of strut 69 and at least strut 69 is attached distally at distal element 66 which is attached to a distal elongate support segment including floppy tip 63.

Figure 7:
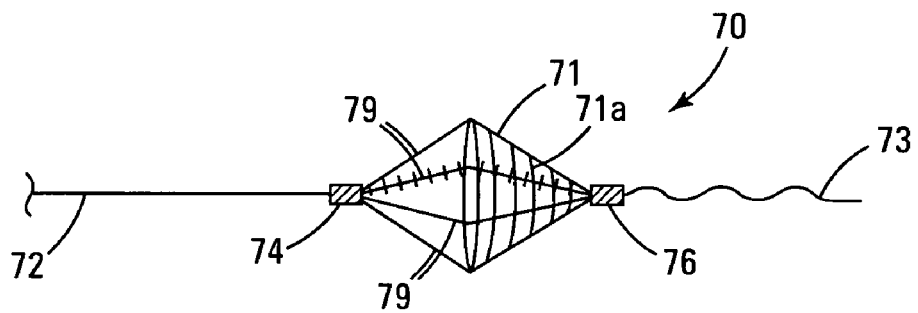

FIG. 7 illustrates device 70 which includes multiple struts 79 having an angular shape. Four struts are shown in the figure although more or fewer could be used. As shown, two of the struts are in the plane of the page; two are perpendicular to the plane of the page, one extending toward the viewer and the other extending away. Struts are biased to expand into contact with a lumen wall. Struts 79 are affixed to proximal and distal elements 74 and 76. Proximal element 74 is fixed to proximal elongate support segment 72. Distal element 76 is fixed to a distal elongate support element including floppy tip 73. A distal portion of struts 79 is covered with filter fabric or filtering polymer film 71a (shown by cross-hatching).

Figure 8:
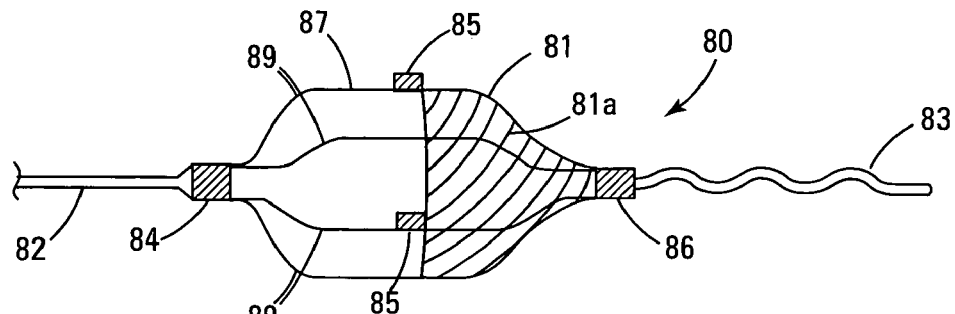

FIG. 8 illustrates device 80, which has a structure similar to the devices shown in FIGS. 6 and 7. Multiple self-expanding curvilinear struts 89 (4 struts are shown in the figure although more or fewer could be used) are affixed to proximal and distal elements 84 and 86. Proximal element 84 is fixed to elongate support member 82. Distal element 86 is fixed to a distal elongate support segment including floppy tip 83. A distal portion of struts 89 is covered with filter fabric or filtering polymeric film 81a (shown by cross-hatching). Optional marker bands 85 are shown on two of the struts, near the edge of the filter fabric. Such bands assist in proper placement of the filter.

Figure 9:
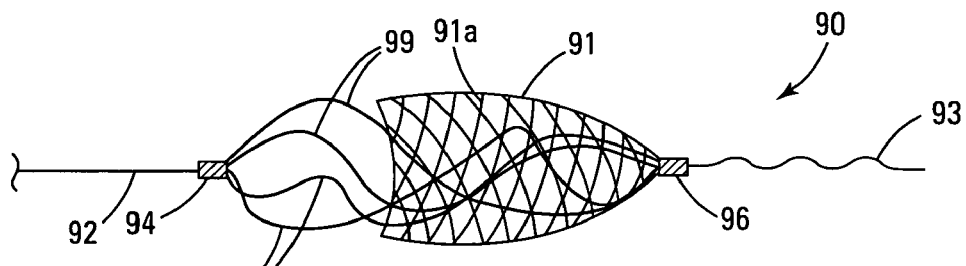

FIG. 9 illustrates device 90, similar to devices described for FIGS. 6 to 8. Multiple struts 99 having a sinusoidal shape (4 struts are shown in the figure although more or fewer could be used) are affixed to proximal and distal elements 94 and 96. Proximal element 94 is fixed to proximal elongate support segment 92. Distal element 96 is fixed to a distal elongate support segment including floppy tip 93. A distal portion of struts 99 is covered with filter fabric or filtering polymeric film 91a (shown by cross-hatching).

Figure 10:
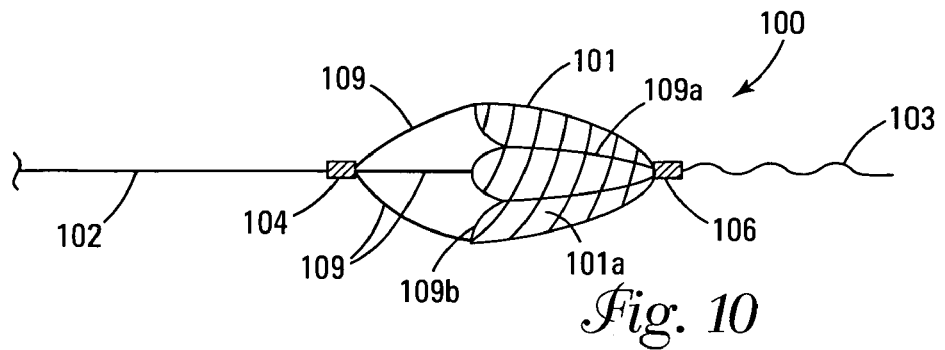

FIG. 10 illustrates device 100, similar to devices described in FIGS. 6 to 9. Multiple struts 109 (4 struts are shown in the figure although more or fewer could be used) are affixed to proximal element 104. Additional struts 109a are provided in the distal portion and are affixed to distal element 106. A segmented circumferential ring 109b is provided to which struts 109 and 109a are attached. Proximal element 104 is fixed to proximal elongate support segment 102. Distal element 106 is fixed to a distal elongate support segment including floppy tip 103. A distal portion of filter 101 is covered with filter fabric or filtering polymeric film 101a (shown by cross-hatching).

Figure 11:
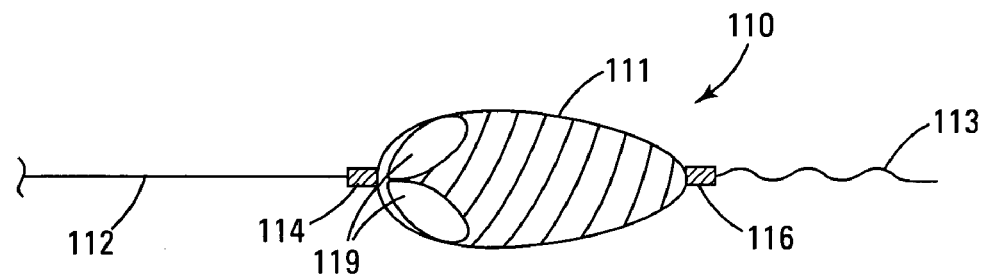
FIG. 11 is a schematic view of an alternate embodiment of the device of this invention showing a filter with proximally facing openings or entry holes.

FIG. 11 shows filter device 110 comprising self-expanding filter 111 having proximal fixed element 114 which is fixed to proximal elongate support segment 112 and distal fixed element 116 which is fixed to a distal elongate support segment including floppy tip 113. Filter 111 is provided with at least one proximally facing entry hole 119. Two holes 119 are shown in the figure. When filter 111 is deployed in a body lumen, fluid flows into the filter through holes 119. The holes in the filter mesh are sufficiently sized to allow the emboli containing fluid to pass through the filter and to trap and retain any emboli or debris within the filter while allowing the fluid to pass therethrough.

Figure 12A:
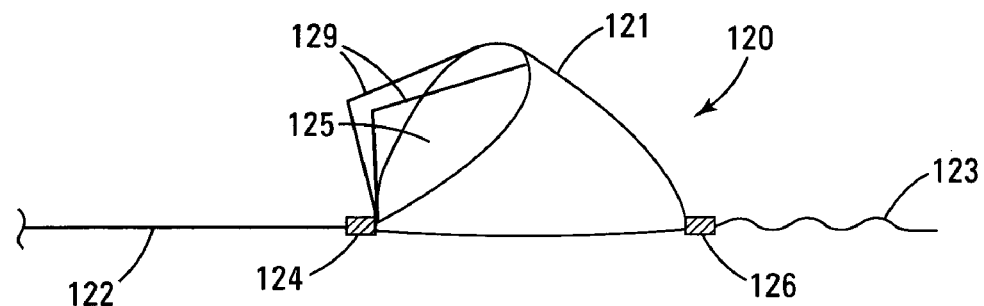
FIGS. 12A and 12B are schematic views of alternate embodiments of the device of this invention wherein the filter has proximal wire segments.

FIG. 12A shows filter device 120, wherein filter device 120 comprises self-expanding filter 121 with distal element 126 affixed to a distal elongate support segment including floppy tip 123. Wire segment 129 extends from fixed proximal element 124 and forms a loop which attaches to the proximal end of the filter and serves to bias the filter and its proximally facing opening 125 in their open or expanded configuration. Wire segment 129 also serves to stabilize proximal element 124 against the lumen wall so as the prevent emboli from bypassing the filter due to motion of wire 122. Such proximal wire loops are more fully described in EP 1 181 900 A2. Filter 121 is attached proximally at fixed element 124 which in turn is affixed to proximal elongate support segment 122.

Figure 12B:
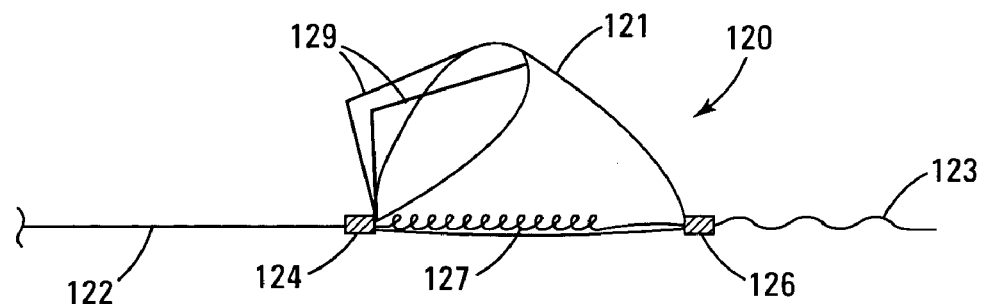

FIG. 12B shows a device similar to that of FIG. 12A except that a flexible coil 127 is attached between proximal and distal elements 124 and 126. The coil serves as a safety wire when fully extended as when the device is being withdrawn proximally during retrieval. The coil also serves to provide transverse flexibility in the region of the filter so as to avoid vessel straightening which is commonly observed in the prior art by the use of straight wires within the filter. Alternatively, the coil could be a braid or series of wire bends that are not coiled. Further, the coil could be an elastomeric polymer or a straight piece of solid or tubular elastomer or could be any other construction having the properties of a coil or elastomer.

Figure 13A:
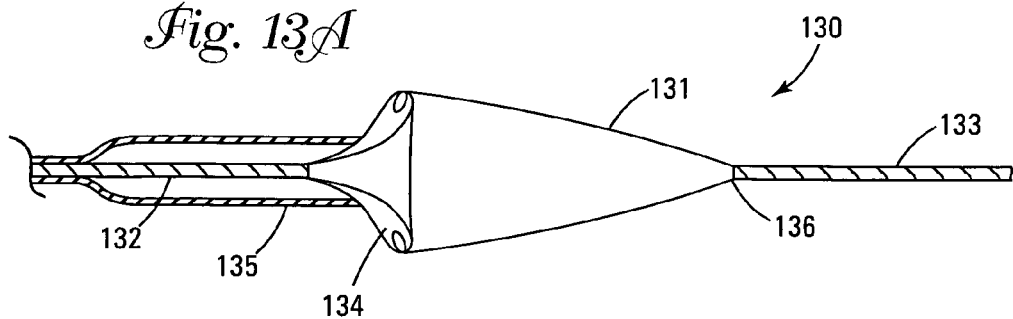
FIG. 13A illustrates a cross-sectional view and FIG. 13B illustrates a perspective view of a further embodiment of this invention.
Figure 13B:
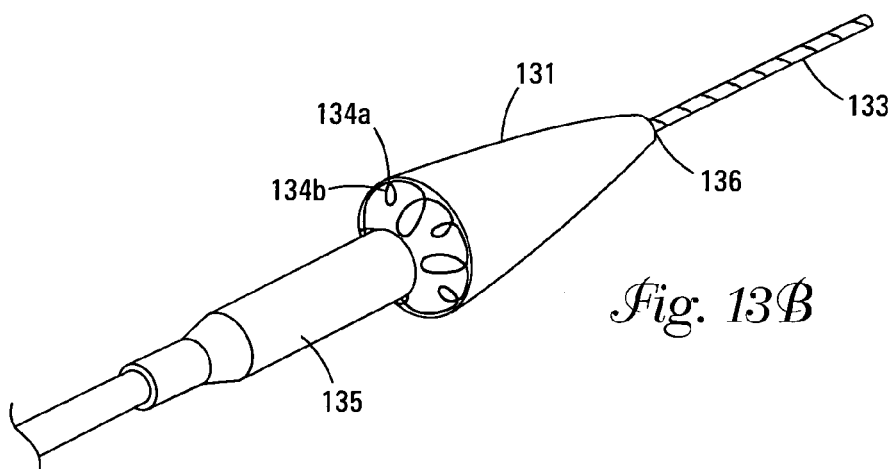
Figure 13C:
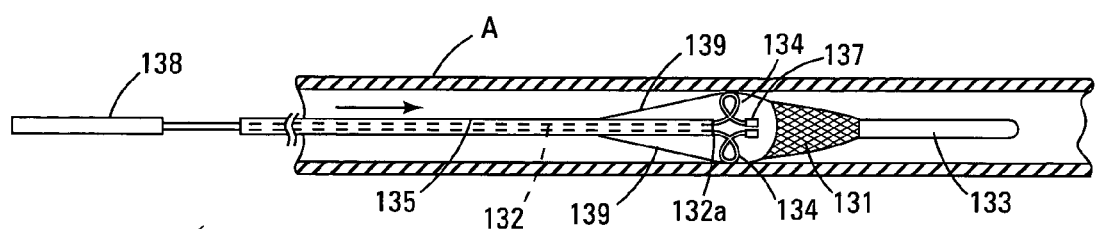
FIG. 13C shows the device of FIG. 13B compressed and loaded into a catheter.

As previously mentioned, this embodiment of the invention which includes the use of a discontinuous guidewire or elongate support member is applicable to a variety of types of functional devices or filters that are mounted on an elongate support members. Another example of such a device is shown in FIGS. 13A to 13C which show a filter device similar to a device described in WO 01/87183 (entitled "Emboli Filter" to Blackledge et al.) with the exception that the elongate support member has been made discontinuous. Filter device 130 comprises filter 131 having a conical shape. At its proximal end, the periphery of the filter is attached to elongate member 132 by means of circumferentially spaced elastic loops 134 having a clover-leaf shape. Preferably, these elastic loops comprise nitinol. They are biased to open radially outwardly, thus serving to hold open the filter. FIG. 13B more clearly illustrates secondary loops 134b that provide a convenient attachment point to the filter. The loops are shown sutured (at suture point 134a) to the filter or may be attached by any suitable method. Unlike the filter device of WO 01/87183 (Blackledge et al.), the present device has a guidewire or elongate member that terminates at the proximal end of the filter, so that no guidewire extends through the filter. The filter has conical tip 136 that is attached to a distal elongate support segment 133. The filter device is shown with hollow tube 135 into which the filter can be retracted for either delivery or removal.

FIG. 13C shows a cross-sectional view of an alternative embodiment of filter device 130 attached to elongate member 132 (shown in phantom), in body lumen A. The filter device is manipulated by handle 138. This is an alternative embodiment to that of FIGS. 13A and 13B, in that loops 134c are of a different shape and the distal ends of the loops are secured via attachment element 137 to the distal end of guidewire 132. The proximal ends of the loops are attached to guidewire 132 at point 132a. Flexible tie strings 139 are attached to filter 131 and to guidewire 132. The tie strings serve to close the filter as the guidewire is being moved proximally, that is, during withdrawal of the filter.

Figure 14A:
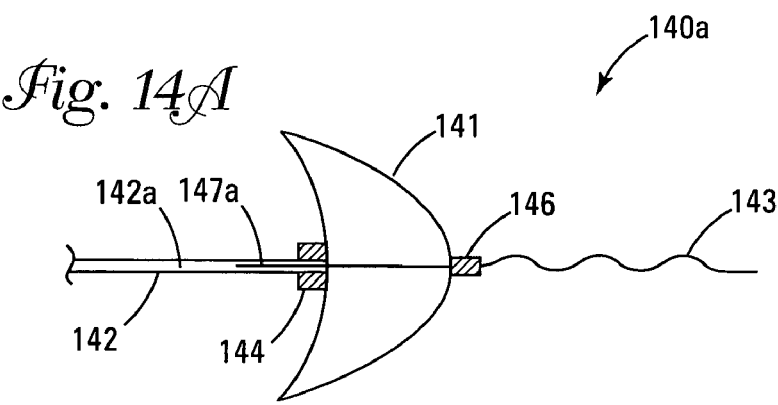
FIGS. 14A to 14D are schematic views of alternate embodiments of the device of this invention wherein a distal elongate support segment is telescoped within the lumen of a proximal elongate support segment.

FIGS. 14A to 14D show various distal protection devices wherein the discontinuous elongate support member includes a distal elongate support segment telescoped within the lumen of a proximal elongate support segment. FIG. 14A shows filter device 140a in which filter 141 is attached to proximal fixed element 144 at proximal elongate support segment 142, which is hollow. Received within lumen 142a of the proximal elongate support segment is a second, smaller diameter wire 147a, which comprises a distal elongate support segment and which extends from within the lumen of the proximal support segment to distal element 146, also attached to the filter and which includes floppy tip 143. Second wire 147a can "telescope" into proximal elongate support segment 142, thus providing for movement of the distal end of the filter but without requiring additional length of the elongate support member as in the prior art device shown in FIGS. 1A and B.

Figure 14B:
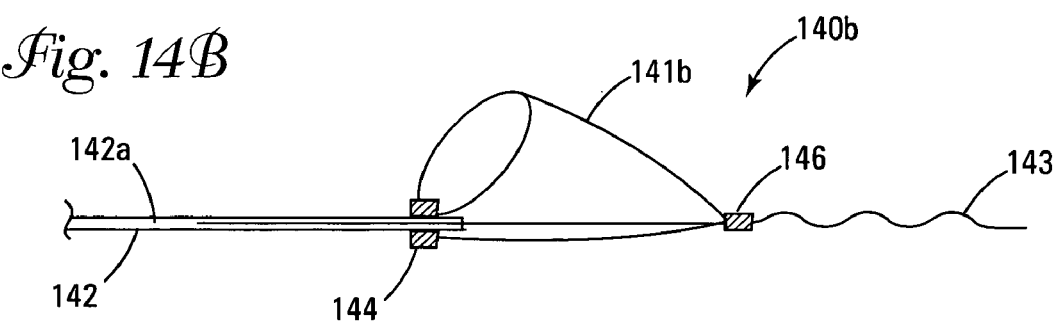
Figure 14C:
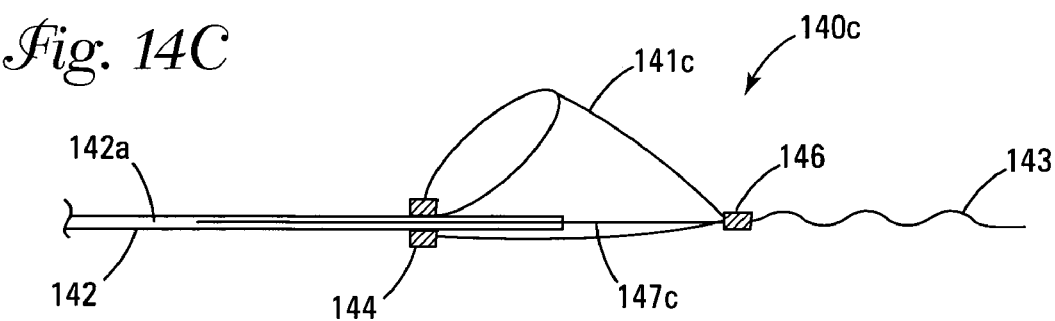
Figure 14D:
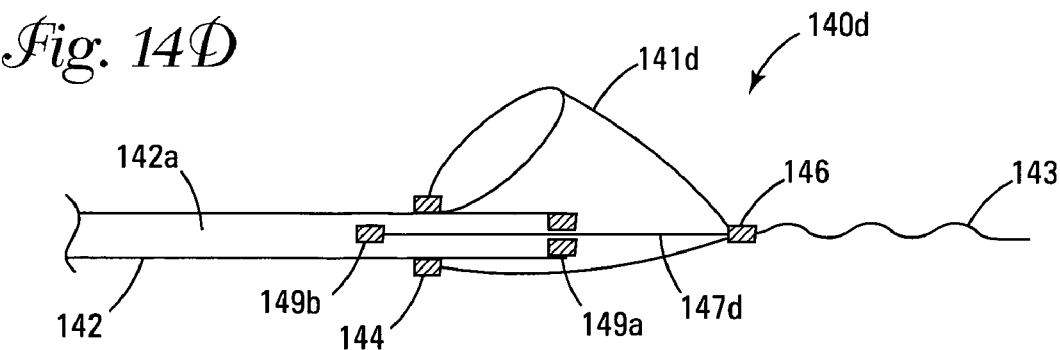

FIG. 14B shows a design similar to FIG. 14A but as applied to a windsock shaped filter 141b. In this case, narrow diameter wire 147b extends from the distal element 146 past the proximal element 144 and into lumen 142a of proximal elongate support member 142. FIG. 14C is an embodiment similar to FIG. 14B where the proximal elongate support member 142 extends into the filter and narrow diameter wire 147c extends through lumen 142a from the distal element past the proximal element. FIG. 14D is similar to the embodiment of FIG. 14C but where the distal end of the proximal elongate support segment 142 has a reduced diameter portion 149a and proximal end 149b of the distal elongate support segment 147d is enlarged to ensure that the support segments do not become disassociated during use.

Figure 15:
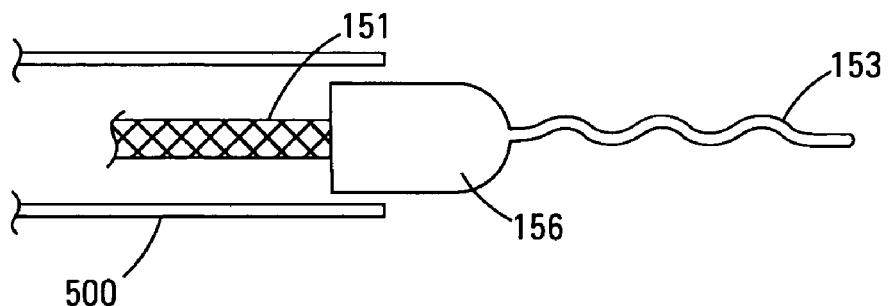
FIGS. 15 to 17 are partial schematic views of alternative configurations of the distal tip applicable to the embodiments of FIGS. 2 to 14.
Figure 16:
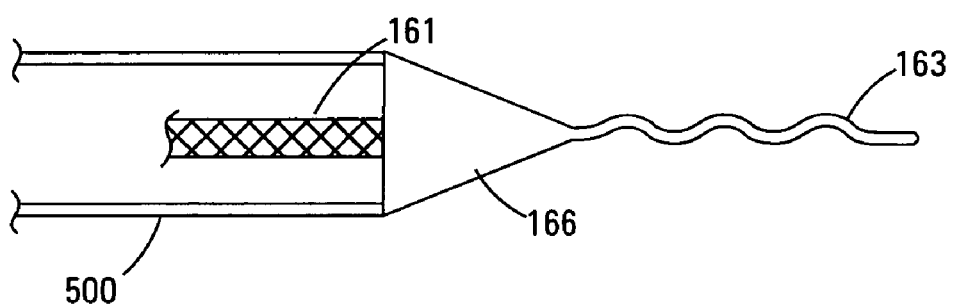
Figure 17:
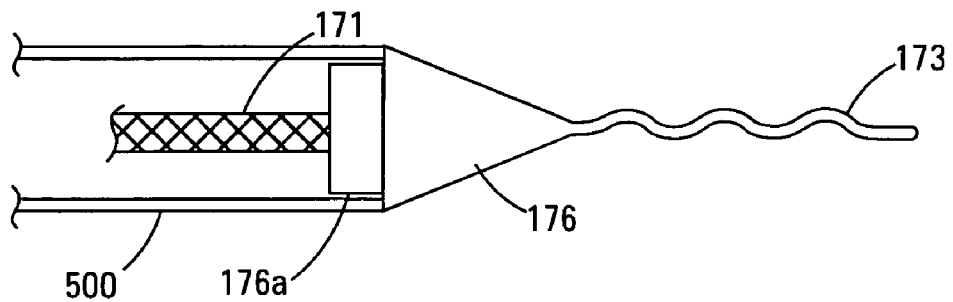

FIGS. 15 to 17 illustrate various distal tip configurations for the distal end of the filters shown in the previous embodiments. These figures show alternative views of the devices of this invention when they are loaded into a delivery catheter before deployment or, alternatively, retrieved by a catheter after they have been used. It is to be understood that these configurations may be used with any of the above-described embodiments.

FIG. 15 illustrates distal element 156 having floppy tip 153 extending from it. Element 156 is attached to the distal end of filter 151. Distal element 156 has a dimension that allows it to enter catheter 500. Its distal portion is tapered, and preferably its proximal edge is chamfered. The advantage of this embodiment is that the protection device can traverse through the lumen of the catheter smoothly, without snagging or hanging up. In FIG. 16, distal element 166 has floppy tip 163 extending from it. Element 166 is attached to the distal end of filter 161. Distal element 166 is larger than catheter 500, and is tapered for ease of movement into a vessel. Specifically, distal element 166 provides a smooth transition between the outside diameter of floppy tip 163 and the outside diameter of catheter 500. FIG. 17 shows distal element 176 having floppy tip 173 extending from it. Element 176 "steps down" at element 176a, which is attached to the distal end of filter 171. Distal element 176a can enter catheter 500 while element 176 cannot. This configuration assures good coaxial alignment between catheter 500 and distal element 176 so that the benefits described in connection with FIG. 16 can be realized in vessel bends or tortuosity.

In a further embodiment the invention is a distal protection device having an elongate support member which carries a functional element such as a filter. In this embodiment the elongate support member is continuous and has a distal portion to which the proximal end of the filter is attached, either fixedly or slidingly. The elongate support member has a distal end which is located proximally of the distal end of the filter at all times during delivery, deployment, use and retrieval of the device. In this embodiment no portion of the elongate support member extends distally of the distal end of the filter.

Examples of this embodiment is shown is FIGS. 18, 19A to 19C and 20. FIG. 18 shows device 180 which includes self-expanding filter 181 carried by a continuous elongate support member 182. The filter has a distal end connected to a fixed distal element 186. Fixed distal element 186 is shaped so that it is atraumatic and is preferably radiopaque. Sliding proximal element 184 is connected to the filter. Elongate support member 182 has an enlarged distal end 185 that cannot pass through proximal element 184 and that cannot pass through mesh 181, to ensure that the filter 181 does not become detached from elongate support member 182 during use, and to prevent the enlarged distal end from passing through or puncturing filter 181. This embodiment is advantageous in that when the filter is in the delivery configuration it is not collapsed over the support member and thus may have a reduced delivery profile. This embodiment also permits a limited range of wire motion independent of filter position, the amount of motion permitted being equal to the distance between the proximal and distal elements minus the length of the enlarged distal end.

Figure 19C:
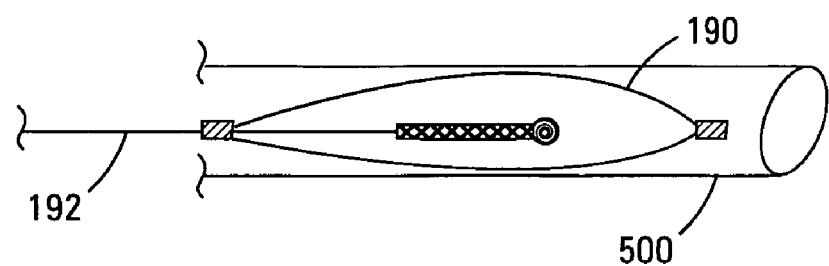
Figure 20:
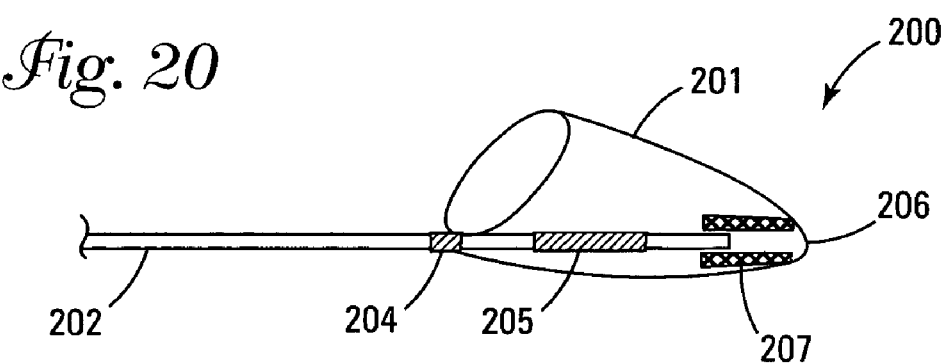
FIG. 20 is a schematic view of another alternate embodiment of the device of this invention having a continuous elongate support member.

It should be understood that it is possible to incorporate the continuous elongate support member feature of the embodiments disclosed in FIGS. 18–20 in any of the devices of FIGS. 2 to 14. In such cases the elongate support member would include only what is disclosed in those figures as the proximal elongate support segment and that no portion of the elongate support member would extend distally of the distal end of the functional element. Devices so constructed can be deployed very distally, for example in native coronary arteries. Very distal deployment of a protection device allows embolic protection of distal lesions during treatment. Distal lesions cannot be treated with prior art devices because their long wire tips impinge on the small diameter vessels thereby preventing very distal advancement and deployment of prior art devices.

FIGS. 19A to 19C show a further embodiment of the invention. In this embodiment the elongate support member is continuous and has a distal end that moves over a range of motion between proximal and distal ends of a functional device. As seen in FIG. 19A, which is a perspective view of device 190, the device includes self-expanding filter 191 which is affixed to proximal slider element 194. Proximal element 194 acts as a marker band and also slides freely over elongate support member 192. Distal element/marker 196 is located at the distal end of filter 191. Elongate support member 192 extends into the filter and terminates at stop 195, which comprises elongate portion 195a and ball tip 195b that is larger than any spaces in the filter mesh. Thus stop 195 cannot move from inside the filter.

FIG. 19B illustrates back-loading the device into catheter 500. Elongate support member 192 is withdrawn proximally until stop 195 engages proximal element 194. Further proximal advancement of elongate support member 192 pulls proximal element, stop, and mesh 191 into catheter. The mesh collapses around stop 195 and ball tip 195b as it is withdrawn into catheter 500. Further proximal withdrawal of elongate support member 192 collapses mesh 191 into the catheter. FIG. 19C shows the distal protection device loaded inside catheter 500 and ready for deployment.

The device is used by advancing the delivery catheter through a body lumen until the distal end of the delivery catheter is at a desired location distal to the treatment site. The filter is then deployed in the body lumen. This can be done by withdrawing the delivery catheter proximally while maintaining the position of the filter or by advancing the filter distally while maintaining the position of the delivery catheter by advancing the elongate support member 192 distally. When the elongate support member 192 is advanced relative to the filter 191, the ball tip 195b will advance distally until contact with the distal end of filter 191 and the distal element 196 is achieved. At this point further advancement of elongate support member 192 relative to filter 191 will urge device 190 out the end of catheter 500. Filter 191 will self-expand into contact with the luminal wall as it is released from catheter 500. In this position emboli and fluid will enter the opening of filter 191. Emboli will be retained in the filter while fluid will pass therethrough. The filter will resist axial or rotational motion of wire 192 because proximal element 194 slides freely over elongate support member 192. Device 190 with emboli contained therein can be recovered by advancing a catheter over elongate support member 192 and withdrawing the elongate support member relative to the filter such that at least the opening of filter 191 is collapsed within the catheter. The catheter can be either the catheter used to deliver the device to the treatment site, a specially designed recovery catheter that may be larger in diameter than the delivery catheter, a treatment catheter such as a PTCA catheter or the like, or another catheter. Once at least the opening of filter 191 is collapsed within a catheter, the catheter can be withdrawn proximally and out of the body.

FIG. 20 shows a filter device wherein the elongate support member is provided with a distal slider element, such as a hypotube or more preferably a tight wound coil. Filter device 200 comprises filter 201 having proximal sliding element 204 and distal element 206. Slider element 204 slides freely over elongate support member 202 which extends into filter 201. Stop 205, such as a wire coil or a hypotube, is affixed to the elongate support member within the filter. Distal slider 207 is configured to accept the distal portion of the elongate support member. Stop 205 and slider 207 are positioned such that the distal end of the elongate support member is always contained within slider 207. Distal slider 207 may be a coil of wire or a hypotube. Distal slider 207 ensures that the filter will be securely carried by the elongate support member while at the same time allow the filter to move longitudinally and rotate axially with respect to the elongate support member.

Although the embodiments disclosed in FIGS. 18, 19A to 19C, and 20 are shown with a continuous elongate support member and have no distal floppy tip, it should be appreciated that these embodiments could be constructed to include a floppy tip such as shown in FIGS. 2 to 17.

The protection device of this invention is particularly useful in the prevention of distal embolization of debris liberated during interventional procedures such as in cardiology, radiology, and neuroradiology procedures.

Although particular embodiments of the invention have been disclosed herein in detail, this has been done for the purposes of illustration only, and is not intended to be limiting with respect to the scope of the appended claims. It is contemplated that various substitutions, alterations, and modifications may be made to the embodiments of the invention described herein without departing from the spirit and scope of the invention as defined by the claims.

What is claimed is:

1. A protection device for use in a body lumen comprising:
   an elongate support member having a proximal end and a distal terminus and a stop positioned proximally of the distal terminus and dividing the elongate support member into proximal and distal portions;
   a proximal slider which is slideable over the proximal portion of the elongate support member, the stop limiting movement of the slider in a distal direction;
   a distal slider which is slideable over the distal portion of the elongate support member; and
   a functional element carried by the elongate support member, the functional element being expandable from a delivery configuration to an expanded deployed configuration when the functional element is deployed in the body lumen, the functional element having a proximal end and a distal end, the proximal end of the functional element being connected to the proximal slider, the distal end of the functional element being connected to the distal slider, the functional element having a body defining a cavity, the distal end of the elongate support member being contained within the cavity and being slideably received by the distal slider when the functional element is in the delivery configuration and when the functional element is in the expanded deployed configuration.

2. The protection device of claim 1 wherein the functional element comprises a filter.

3. A protection device for use in a body lumen comprising:
   an elongate support member having a proximal elongate segment and a distal elongate segment, the proximal and distal elongate segments each having a proximal end and a distal terminus, the distal terminus of the proximal elongate segment being enlarged;
   a slider which is slideable over the proximal elongate segment, the enlarged distal terminus of the proximal elongate segment limiting movement of the slider in a distal direction; and
   a functional element carried by the elongate support member, the functional element being expandable from a delivery configuration to an expanded deployed configuration when the functional element is deployed in the body lumen, the functional element having a proximal end and a distal end, the proximal end of the functional element being connected to the slider, the functional element having a body defining a cavity, the distal terminus of the distal elongate segment being contained within the cavity.

4. The protection device of claim 3 wherein the functional element comprises a filter.

* * * * *